United States Patent [19]

Macchiarulo et al.

[11] Patent Number: 5,351,530
[45] Date of Patent: Oct. 4, 1994

[54] METHOD AND APPARATUS TO CHECK THE ACCEPTABLENESS OF THE STATE OF WEAR IN THE COVERING FABRIC OF A DRIVING BELT

[75] Inventors: Vincenzo Macchiarulo, Pescara; Tommaso DiGiacomo, Guardiagrele, both of Italy

[73] Assignee: Pirelli Trasmissioni Industriali S.p.A., Chieti, Italy

[21] Appl. No.: 44,045

[22] Filed: Apr. 8, 1993

Related U.S. Application Data

[62] Division of Ser. No. 801,575, Dec. 6, 1991, Pat. No. 5,212,982.

[30] Foreign Application Priority Data

Dec. 11, 1990 [IT] Italy ............... 22335A/90

[51] Int. Cl.$^5$ ............................................. G01M 15/00
[52] U.S. Cl. ................................... 73/118.1; 474/268
[58] Field of Search .................. 73/118.1, 775, 776; 324/701, 206; 474/268; 340/438

[56] References Cited

U.S. PATENT DOCUMENTS

| | | | |
|---|---|---|---|
| 3,541,437 | 11/1970 | Ahrweiler | 324/701 |
| 3,576,425 | 4/1971 | Owen . | |
| 3,636,442 | 1/1972 | Doi | 324/701 |
| 4,106,005 | 8/1978 | Asakawa | 324/206 |
| 4,235,091 | 11/1980 | Takano et al. . | |
| 4,296,855 | 10/1981 | Blalock | 198/502 |
| 4,300,094 | 11/1981 | Piso | 324/701 |
| 4,371,363 | 2/1983 | Cicognani et al. . | |
| 4,678,455 | 7/1987 | Hollaway, Jr. | 474/268 X |
| 4,742,295 | 5/1988 | Nahman et al. . | |
| 4,983,814 | 1/1991 | Ohgushi et al. | 219/545 |

FOREIGN PATENT DOCUMENTS

| | | |
|---|---|---|
| 0082476 | 6/1983 | European Pat. Off. . |
| 0490838 | 6/1992 | European Pat. Off. . |
| 1918337 | 9/1970 | Fed. Rep. of Germany ...... 324/701 |
| 3238089 | 4/1984 | Fed. Rep. of Germany . |
| 3308793 | 9/1984 | Fed. Rep. of Germany . |
| 3532795 | 4/1986 | Fed. Rep. of Germany . |
| 1522852 | 4/1968 | France .............. 324/701 |
| 2149045 | 3/1973 | France . |
| WO8302162 | 6/1983 | PCT Int'l Appl. . |
| 541743 | 3/1977 | U.S.S.R. . |

*Primary Examiner*—Robert Raevis
*Attorney, Agent, or Firm*—Stevens, Davis, Miller & Mosher

[57] ABSTRACT

A method and apparatus for carrying out the checking of the state of wear of a covering fabric in a driving belt (2) mounted on a plurality of pulleys (3, 4, 5) by measuring the electric resistance variations of the belt fabric. The apparatus provides that at least two of the pulleys (3, 4, 5) should be electrically insulated with respect to each other and connected to an electric circuit (20) designed to apply an electric voltage to said pulleys in order to carry out the measuring of the electric resistance of the fabric exhibited by belt stretches (A, B) comprised between the pulleys themselves. The electric resistance thus found lends itself to be compared with predetermined resistance values corresponding to different states of wear of the belt (2) fabric. The work surface of the belt (2) is coated with an electrically conductive fabric (12) acting by contact on the pulleys (3, 4, 5) and having characteristics of tensile strength.

14 Claims, 2 Drawing Sheets

METHOD AND APPARATUS TO CHECK THE ACCEPTABLENESS OF THE STATE OF WEAR IN THE COVERING FABRIC OF A DRIVING BELT

This is a divisional of application Ser. No. 07/801,575 filed Dec. 6, 1991, now U.S. Pat. No. 5,212,982.

BACKGROUND OF THE INVENTION

1. Field of the Invention

The present invention relates to a method and apparatus to check the acceptableness of the state of wear in the covering fabric of a driving belt, said apparatus being of the type comprising:

- an electrically conductive bearing structure;
- at least a first and a second electrically conductive pulleys rotatably engaged to said bearing structure;
- a driving belt operatively engaged on said pulleys and having a body provided with a reinforcement fabric on the work surface thereof designed to act in contact with said pulleys.

The method and apparatus in question can be used on driving belts of different kinds such as for example toothed belts, V-shaped belts, flat grooved belts and so on.

In the course of the present description reference will be particularly made, by way of non-limiting example only, to the use of the inventive method and apparatus for carrying out the checking of the state of wear in toothed belts.

2. Prior Art

It is known that driving belts and in particular toothed belts are used to transmit rotational movements from a toothed driving pulley to toothed driven pulleys.

Toothed driven pulleys control the movement of the mechanical members that, due to their operation, need to rotate in timed relationship with other mechanical members taking in rotation of the toothed driving pulley.

The concerned toothed belts substantially consist of a main body made of elastomeric material in which inextensible cords circumferentially disposed in side by side relation with respect to one another, are buried.

Internal to the annular configuration of the belt there is a number of teeth circumferentially distributed according to a predetermined pitch, which define the work surface of the belt and are designed to mesh with corresponding toothings offered by the pulleys.

The teeth, formed from part of the elastomeric material belonging to the main body, are greatly submitted to stresses, due to the thrust action transmitted to them by the toothing of the driving pulley and the thrust action they apply to the toothings of the driven pulleys.

In order to give the teeth the necessary strength so that they may withstand said stresses and the resulting wear phenomena, in many cases the work surface of the belt is covered with a reinforcing fabric also performing the function of protecting the elastomeric material against the action of chemical substances or other external agents with which the belt could be brought into contact.

This reinforcing fabric is directly exposed on the inner surface of the belt and is therefore the only element acting in contact with the pulleys.

As can be easily understood, during the belt operation the fabric will be subjected to a wear action that will bring about a gradual reduction in the thickness of the same and, as a result, a reduction in its capability of withstanding stresses.

This wear action, if extended in time, can lead to the reinforcing fabric tearing and therefore to the breakage of some teeth or even of the belt.

In most cases the foregoing inconvenience would cause important damages to the mechanical members driven by the belt in timed relationship.

Presently the only method enabling the state of wear or the impending breakage of a toothed belt to be verified is visual control.

Said visual control, in almost all of the cases, can be made only by dismantling the belt from the equipment to which it belongs, which involves the removal of many mechanical parts necessary to the operation and protection of the belt.

Another solution consists in periodically replacing the driving belts at regular intervals, but in this case belts which are not yet completely worn are almost always discarded.

In order to avoid the unexpected breakage of a belt it has been found possible to resort to a method and apparatus for checking the state of wear in the reinforcement fabric of a belt by verifying the electrical resistance variations in the fabric comprising conductive fillers.

SUMMARY OF THE INVENTION

The present invention relates to a method of checking the acceptablenes of the state of wear in the reinforcement fabric of a driving belt operatively engaged between at least one pulley and a second pulley and having a body provided with said reinforcement fabric on a work surface thereof designed to act in contact with the pulleys, said method comprising the following steps carried out in the presence of said belt the fabric of which is associated with electroconductive fillers:

- applying a predetermined electric voltage between at least the first pulley and the second pulley in order to achieve an electric current passage along the belt stretches "A", "B" comprised between said first and second pulleys, said pulleys being electrically insulated with respect to each other;
- measuring one electric resistance value offered by the belt stretches "A", "B" on passing of said electric current;
- comparing said first resistance value with a predetermined electric resistance value corresponding to a given state of wear of the belt fabric.

In accordance with a further aspect of the invention an apparatus is provided for checking the acceptableness of the state of wear in the reinforcement fabric of a driving belt of the type comprising:

- an electrically conductive bearing structure;
- at least a first and a second pulleys which are electrically conductive and rotatably engaged to said bearing structure;
- a driving belt operatively engaged on said pulleys and having a body provided with a reinforcement fabric on the work surface thereof designed to act in contact with said pulleys, said method further comprising:
- an electric circuit having the respective poles electrically connected to the first pulley and second pulley in order to apply electric voltage to the belt stretches "A", "B" kept taut between said pulleys, said at least first and second pulleys being electrically insulated with respect to each other;

a measuring instrument for the electric resistance, associated with said electric circuit and designed to carry out the measuring of the electric resistance exhibited by the belt stretches "A", "B", conductive fillers being associated with said reinforcement fabric, designed to make said fabric electrically conductive;

electronic means designed to compare the electric resistance values detected by said instrument with predetermined values corresponding to given wear conditions of the belt;

alarm means designed to signal when said electric resistance values correspond to said predetermined values.

BRIEF DESCRIPTION OF THE DRAWINGS

Further features and advantages will become more apparent from the detailed description of a preferred embodiment of a method and apparatus for checking the acceptableness of the state of wear in a driving belt, given hereinafter by way of non-limiting example with reference to the accompanying drawings, in which.

DESCRIPTION OF THE PREFERRED EMBODIMENT

Figure 1:
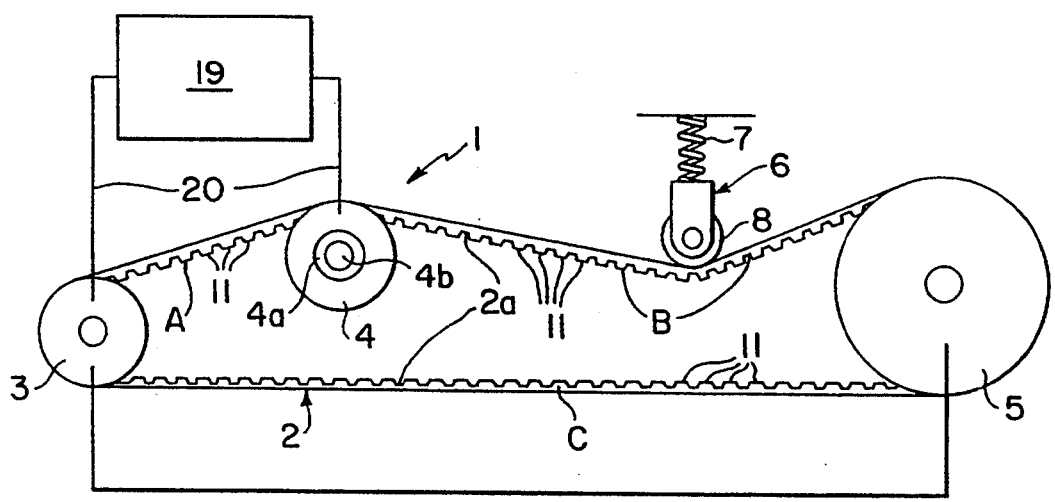
FIG. 1 is a diagrammatic view of the apparatus of the present invention.

Referring particularly to FIG. 1, an apparatus for checking the acceptableness of the state of wear in a driving belt has been generally identified by reference numeral 1.

Apparatus 1 acts on a driving belt 2 which in the example shown is of the toothed type, operatively mounted to at least a first and a second pulleys 3, 4 rotatably engaged with a bearing structure not shown as it is known per se and not of importance to the ends of the invention.

In the embodiment shown a third pulley 5 is also provided and it is operable in rotation by a motor so as to transmit, through the belt 2, a rotatory movement to the first and second pulleys 3, 4.

Still by way of example only, an idler roller 6 can also be provided and it mainly comprises a spring member 7 acting on a wheel 8 so as to exert an elastic tensioning action on the belt 2.

To the ends of the present invention it is important to note that pulleys 3, 4 and 5 as well as the above mentioned bearing structure are conventionally made of electrically conductive metal material. Pulleys 3, 4, 5 are therefore in a state of electric contact with the work surface 2a of belt 2.

Advantageously, in accordance with the present invention, the first and second pulleys 3, 4 are provided to be electrically insulated with respect to each other. For the purpose, the second pulley 4 is electrically insulated from the bearing structure for example by interposing a bush 4a made of insulating material between the pulley and a shaft 4b rotatably engaging said pulley to the bearing structure.

As diagrammatically shown in FIG. 1, the first and third pulleys 3 and 5 are on the contrary electrically connected to each other, through the bearing structure.

Figure 3:
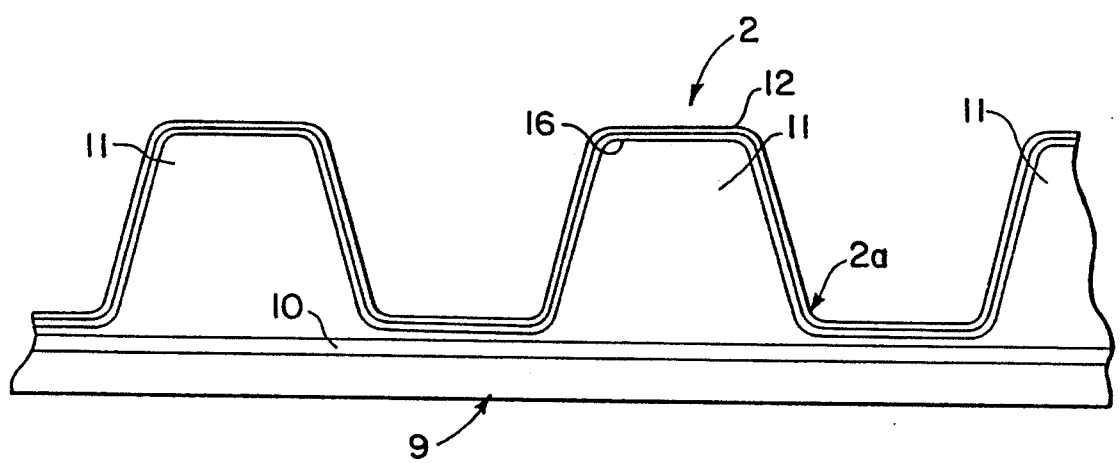
FIG. 3 is an enlarged side view of a portion of a toothed belt.
Figure 4:
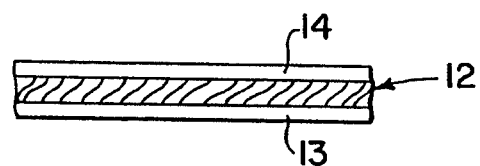
FIG. 4 is an enlarged diagrammatic view of the elements forming the reinforcement fabric in the belt shown in FIG. 3.
Figure 5:
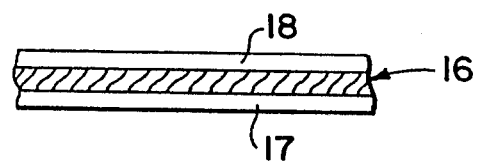
FIG. 5 is an enlarged diagrammatic view of the elements forming the insulating material in the belt shown in FIG. 3.

Still in a manner known per se, the belt 2 to which apparatus 1 is applied comprises a main body 9 made of elastomeric material, into which inextensible cords are buried (FIG. 3).

The main body 9, of annular form, has a number of teeth 11 on the inner face thereof which are spaced apart from each other by the same distance and substantially define said work surface 2a designed to act on the toothed pulleys 3, 4 and 5 by contact.

The work surface 2a with the respective teeth 11 is structurally reinforced and is made conductive by a reinforcement fabric 12 directly exposed to the outside of said work surface.

In accordance with the present invention, the reinforcement fabric 12, before being associated with the toothed belt 2, is submitted to a particular process aiming at giving it the desired electric conductivity for the purposes to be specified later.

In greater detail, applied to the reinforcement fabric 12 is one layer of electrically conductive material 13 and a second layer of electrically conductive material 14, both consisting of a polychloroprene-base polymer containing conductive fillers to predetermined amounts. As an alternative solution to the polychloroprene-base polymer, all other base polymers adapted for driving belts can be used, for example hydrogenated cyanocarbon-based polymers (HNBR) or special chlorosulfonates (ACSM).

The conductive fillers preferably consist of a type of carbon black, such as furnace black commercially available for example under the trade name "Vulcan P".

Fillers can have sizes of 200 Angstrom.

The conductive features are defined by the following data:

surface area 149 m$^2$/g measured according to specifications ASTM.D 3037 iodine number 168 mg/g measured according to specifications ASTM.D 1510

DBP absorption 113 mg/100 g measured according to specifications ASTM.D 2414.

The first layer disposed towards the belt body 9, is formed with a mix mainly containing carbon black (50 parts by 100 parts of polymer) and also containing vulcanizing, antioxidant and plasticizing ingredients to lower amounts.

The second electrically conductive layer 14, exposed on the work surface 2a, is in turn formed with a mix mainly containing self-lubricating graphite (60 parts by 100 parts of polymer), carbon black (20 parts by 100 parts of polymer) and also containing aromatic oils and antistaticizing ingredients to lower amounts.

On preparing the reinforcement fabric 12, the first step is a soaking step and consists in dipping said fabric into a tank containing the same mix, suitably diluted, as used to make the first layer 13. Subsequently the reinforcement fabric 12 is held in appropriate furnaces promoting the evaporation of the diluent amount present in the mix used for the fabric soaking.

The amount of mix permeating through the fabric due to the soaking step is in the range of 25 to 100 g and preferably in the range of 45 to 75 g per square meter of processed reinforcement fabric 12.

At the end of the above operation the first electrically conductive layer 13 is applied to the reinforcement fabric 12. The amount of the material deposited on the reinforcement fabric 12 for the formation of the first layer 13 is comprised between 20 and 90 g and preferably between 45 and 65 g per square meter of treated fabric.

Subsequently the second electrically conductive layer 14 is applied.

The amount of material deposited during this step ranges between 20 and 60 g and preferably between 30 and 40 g per square meter of treated fabric 12.

Said layers 13, 14 are applied with the aid of an adjustable-in-height doctor by virtue of which it is possible to coat the above mixes according to very accurate thicknesses.

At the end of the above treatment, the ratio between the electric resistance of the main body 9 and the electric resistance of the reinforcement fabric 12 is provided to be at least equal to 50.

If the conductivity of the elastomeric material used in making the main body 9 is high to the point that it would be difficult to achieve the above ratio value, the application of the reinforcement fabric could take place after interposing an insulating material generally denoted by 16 which, due to its insulating properties, would make the reinforcement fabric 12 electrically independent of the body itself.

Before being associated with the main body 9, the insulating fabric 16 undergoes the application of a first and a second insulating layers 17, 18 to the opposite faces thereof. The material used to make said insulating layers 17, 18 substantially consists of a polychloroprene-based mix containing light fillers, coarse black used in this case as colorant and vulcanizing and antioxidant substances.

The application of the insulating layers 27, 28 is carried out after soaking of the insulating material 18 by dipping it into another tank containing the same mix as that used for the insulating layers 17, 18, conveniently diluted.

As previously stated with reference to the reinforcement fabric 12, the elimination of the diluent from the insulating material 16 takes place with the aid of a furnace.

The amount of the third mix introduced into the insulating fabric 16 as a result of the soaking operation is in the range of 20 to 75 g and preferably of 25 to 55 g per square meter of treated fabric.

Subsequently the application of the insulating layers 17, 18 is carried out still through coating by means of a doctor of adjustable height.

The applied mix amount for the accomplishment of each insulating layer 17, 18 is comprised between 25 and 55 g per square meter of treated insulating fabric 16.

The binding between the conductive reinforcement fabric 12 and the insulating fabric 16, as well as the application of said fabrics to the main body 9 of belt 2 takes place during the manufacture of the toothed belts according to known and conventional procedures which are not further described herein.

The apparatus 1 puts into practice a method that, in accordance with the present invention, is based on the principle of detecting the electric resistance value exhibited by the belt 2 and comparing it with predetermined resistance values corresponding to given wear conditions of the belt.

Figure 2:
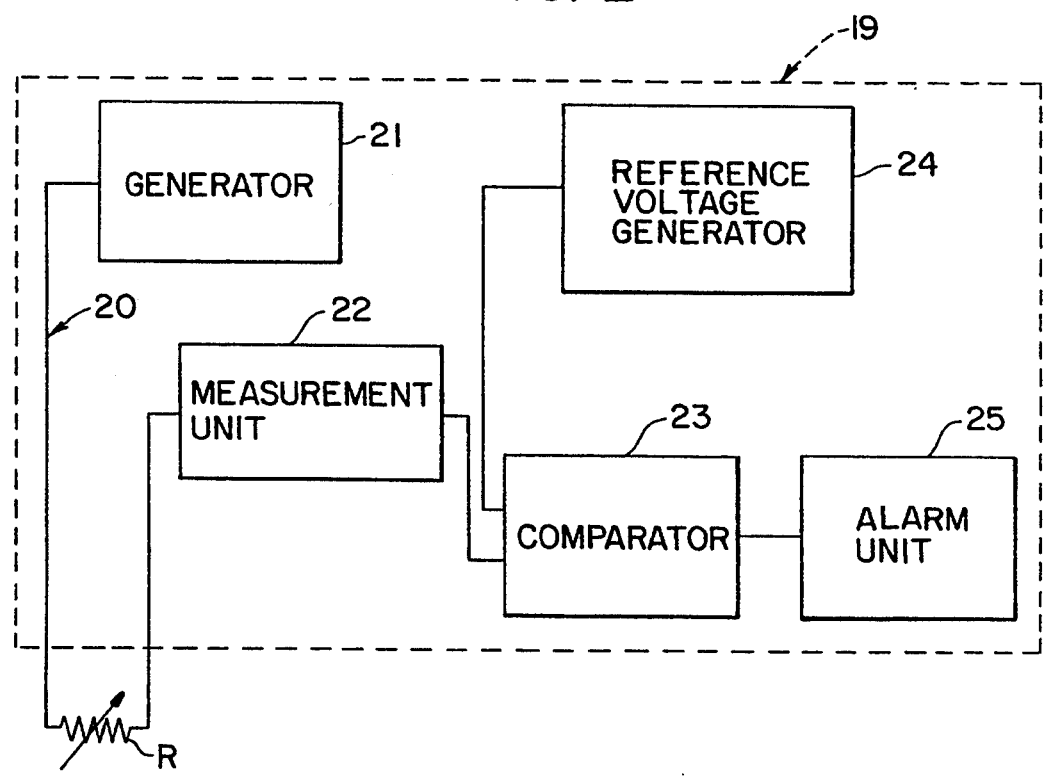
FIG. 2 is a block diagram showing a measuring and checking unit belonging to the apparatus of FIG. 1.

The detection of the electric resistance in belt 2 is carried out by a control unit generally identified by 19 in FIG. 1 and shown in detail in FIG. 2. Said unit by an electric circuit 20 fed by an electric generator 21, applies an electric potential difference between the bearing structure and the electrically insulated second driven pulley 4.

The electric circuit 20 in the embodiment shown is connected at its negative pole to the bearing structure and consequently to the first and third pulleys 3 and 5 and at its positive pole to the second pulley 4.

Under this situation, the belt 2 is passed through by a current flow at its first and second stretches denoted by "A" and "B" respectively and defined between the first and second pulleys 3, 4 and between the second and third pulleys 4, 5.

These belt stretches will behave as two resistors connected in parallel to the electric circuit 20 and will give rise to a resultant resistance denoted by "R" in FIG. 2, the value of which varies depending upon the state of wear of the belt and in particular of the conductive reinforcement fabric 12.

It is in fact noted that the current passage along stretches "A" and "B" in belt 2 takes place in the section area defined by the conductive reinforcement fabric 12 which is the only belt component directly in contact with pulleys 3, 4 and 5. As a result, due to the prolonged use of the belt the reinforcement fabric 12 will become worn thereby progressively losing the conductive fillers associated therewith during the manufacture, as previously described. It can be easily understood that as the conductive fillers are lost the electric resistance of belt 2 increases.

The electric circuit 20 leads to an electric measurement instrument 22 adapted to detect the value of the resultant electric resistance "R". Preferably the measuring instrument 22 consists of a voltmeter and enables the value of the resultant resistance "R" to be drawn based on the voltage measured downstream of the belt stretches "A" and "B", the voltage applied by generator 21 being known.

The measuring instrument 22 is connected to a comparator 23 designed to compare the voltage value detected by the measuring instrument 22 and therefore the resultant resistance "R" value with a predetermined resistance value, entered by means of a voltage generator 24 transmitting an electric signal having a predetermined voltage to the comparator itself.

Preferably the above signal corresponds to the maximum acceptable wear condition of belt 2 and substantially corresponds to ten times the resultant resistance value "R" exhibited by belt 2 when new.

If said comparison gives a result according to which the resistance value "R" supplied by belt 2 is equal to or higher than the predetermined value, comparator 23 will trigger the alarm means 25 in order to generate a signal informing the operator that the belt 2 is likely to break very soon.

The application of the potential difference and the detection of the electric resistance "R" are preferably carried out while the belt is at a standstill and therefore when the apparatus interlocked to the belt is not in operating condition.

Preferably comparator 23 should carry out the checking of the belt wear each time said apparatus is stopped and/or is about to be started. Preferably the method is put into practice when the belt is not running.

Comparator 23 may also carry out, if desired, further controls on the regularity and progressivity of the belt wear, together with the control of the state of wear of belt 2.

To this end, after the belt 2 has been operated and stopped again, comparator 23, then perform a second control of the state of wear performed in the same manner as previously described, and carries out a comparison between a second resistance value "R" resulting from said second control and the first resistance value "R" which had been detected during the previous control on the state of wear.

Still by action of comparator 23, the difference between the first and second resistance values "R" is detected. This difference is afterwards compared with a previously entered difference value corresponding to a normal wear increase of belt 2. The previously entered resistance value can optionally be established by storing in comparator 23 the difference value or the average of the difference values found during the previous control steps.

If the difference value detected substantially corresponds to the previously entered difference value, the belt 2 is getting worn following a normal increasing development.

If, on the contrary, the difference value detected exceeds the previously entered value, the belt 2 is getting worn more quickly than it should, for example due to factors unrelated to the belt 2 such as a bad operation or wear of the pulleys, or to damages produced on the belt itself as a result of bad operation of the mechanical parts adjacent to it.

In this case comparator 23 operates the alarm means that will inform of the impending belt breakage.

By way of example only, data resulting from wear-checking experimental tests carried out by the method and apparatus of the invention on toothed belts intentionally damaged with localized abrasions or cuts at the reinforcement fabric 12 will be hereinafter set forth.

Belts 2 on which said experimental tests have been carried out are of the type described in U.S. Pat. No. 4,371,363. The tooth pitch 11 of this type of belt is equal to 9.525 mm and the width is of 19 to 20 mm.

The following resistance values per length unit have been detected on this type of belt in the absence of localized abrasions or cuts on the reinforcement fabric:
   the new belt: 8.756 Kohm×cm;
   the belt after 300 hours of operation: 126.3 Kohm×cm.

It is to be pointed out that these values have been established by applying two terminals at the ends of a length of slit belt and connecting said terminals to the poles of the electric circuit 20 belonging to unit 19.

Said terminals are shaped as a pulley tooth and act by contact on the belt length ends with a pressure between 6 and 7 kg/cm$^2$.

During the tests the damaged belts have been mounted on pulleys substantially disposed as shown in FIG. 1, having the following geometrical parameters:
   length of stretch "A": 117.3 mm;
   length of stretch "B": 158.4 mm;
   length of stretch "C": 298.9 mm;
   winding arc on the first pulley 3: 83.6 mm;
   contact area on the first pulley 3: 1198 mm$^2$;
   number of teeth engaged to pulley 3: nine;
   winding arc on the second pulley 4: 25.2 mm;
   contact area on the second pulley 4: 399 mm$^2$;
   number of teeth engaged to pulley 4: three;
   winding arc on the third pulley 5: 232 mm;
   contact area on the third pulley 5: 3327 mm$^2$;
   number of teeth on pulley 5: twenty-five.

Test results:
   resultant resistance "R" with an unworn belt: 135 Kohm;
   with an abrasion in stretch "A": 238 Kohm;
   with an abrasion in stretch "B": 208 Kohm;
   with an abrasion in stretch "C": 135 Kohm;
   with an abrasion in stretch "A" and one in stretch "B": 2.2 Mohm;
   with an abrasion in stretch "B" and one in stretch "C": 275 Kohm;
   with two abrasions in stretch "C": 135 Kohm.

The term "abrasion" as herein used means a state of wear capable of producing a variation in the fabric thichness to a varying degree until the appearance of the fabric or the underlying body.

Resultant resistance "R" with a cut in stretch "A": 310 Kohm;
   with a cut in stretch "B": 220 Kohm;
   with a cut in stretch "C": 135 Kohm.

The term "cut" as herein used means a true break of continuity in the conductive surface.

In accordance with the invention all risks of sudden and unforeseen breakage of the belt are substantially reduced and almost always completely prevented by verifying the progressive state of wear of the reinforcement fabric through the detection of the electric resistance variations in the two belt stretches put in parallel to each other.

It has been found that the aimed result can be reached by dividing the belt into two stretches.

In fact, as can be seen in the preceding example, the signal relating to the electric resistance variations that involve one of the belt stretches in a practically localized manner is about 1.5 times the signal relating to unworn stretches, whereas the signal relating to the simultaneous variation of electric resistance in the two stretches is greatly higher, at least about 10 times the signal relating to the localized wear of one belt stretch only.

Practically in the first case the local wear and/or solution of continuity in the surface of one of the stretches can be compensated for by the mechanical strength of the parts still present in the fabric and therefore the corresponding signal transmitted to the user will indicate an initial state of wear for which an immediate intervention may not be needed.

In the second case the important increase in the resulting signal, having overall electric resistance values ten times greater than in the first case, will indicate a wear and/or the solution of continuity of the conductive surface which is no longer localized but extended to an important part of the belt, and therefore a situation of overall mechanical strength that could become inappropriate within a very short period of time and bring to the belt breakage.

If the belt wear increases too much, the apparatus 1 informs the operator that an imminent belt breakage is likely to occur, maybe due to causes unrelated to the belt itself.

Obviously many modifications and variations can be made to the invention as conceived, all of them falling within the scope of the inventive idea characterizing it; for example the method described in connection with a motionless belt can also be put into practice with a running belt and both measurements will be capable of comparison with predetermined reference parameters.

What is claimed is:

1. A driving belt comprising:
   an elastomeric body;
   at least one reinforcement fabric applied on a working surface of the elastomeric body;
   electroconductive fillers incorporated in the reinforcement fabric in an amount sufficient to cause a ratio between an initial electric resistance of the belt body when unworn and said at least one reinforcement fabric to be at least equal to 50:1.

2. A driving belt as claimed in claim 1 further comprising an insulating layer interposed between said reinforcement fabric and said elastomeric body.

3. A driving belt as claimed in claim 1, wherein said reinforcement fabric comprises:
   a first layer of polymeric material made of carbon black and vulcanizing, antioxidant and plasticizing substances, said first layer being applied to the reinforcement fabric surface facing said belt body;
   a second layer of polymeric material made of graphite, carbon black, antistaticizing agents and aromatic oils, said second layer being applied to the reinforcement fabric surface forming the working surface.

4. A driving belt as claimed in claim 1 wherein said reinforcement fabric comprises:
   a first fabric containing a first electroconductive mix;
   a first layer made of the first electroconductive mix and applied to a surface of a first fabric facing said belt body;
   a second layer made of a second electroconductive mix and applied to a surface of a first fabric forming the working surface.

5. A driving belt as claimed in claim 4 wherein said first electroconductive mix contains 50 parts of carbon black to 100 parts of polymer, as well as vulcanizing, antioxidant and plasticizing agents.

6. A driving belt as claimed in claim 4 wherein said second electroconductive mix contains 60 parts of self-lubricating graphite to 100 parts of polymer, 20 parts of carbon black to 100 parts of polymer, as well as antistaticizing agents and aromatic oils.

7. A driving belt as claimed in claim 4 wherein said first electroconductive mix is a polychloroprene-base mix.

8. A driving belt as claimed in claim 4 wherein said second electroconductive mix is a polychloroprene-base mix.

9. A driving belt comprising:
   an elastomeric body;
   at least one reinforcement fabric applied on a working surface of the elastomeric body;
   electroconductive fillers incorporated in said at least one reinforcement fabric;
   an insulating layer interposed between said at least one reinforcement fabric and said elastomeric body.

10. A driving belt as claimed in claim 9, wherein said insulating layer comprises:
    a second fabric containing a third insulating mix; and
    a third and a fourth layers made of said third insulating mix and applied on opposite surfaces of said insulating layer.

11. A driving belt as claimed in claim 10 wherein said third insulating mix is a polychloroprene-base mix containing light fillers, coarse black used as colorant, and vulcanizing and antioxidant substances.

12. A driving belt as claimed in claim 10 wherein the third insulating mix in the second fabric is in an amount comprised between 20 g and 75 g per square meter of treated fabric.

13. A driving belt as claimed in claim 12 wherein the third insulating mix in the second fabric is in an amount comprised between 25 g and 55 g.

14. A driving belt as claimed in claim 10 wherein the third insulating mix which forms the third and the fourth layers is in an amount comprised between 25 g and 55 g per square meter of treated fabric.

* * * * *